United States Patent [19]

Wright et al.

[11] Patent Number: 5,650,170
[45] Date of Patent: Jul. 22, 1997

[54] DOSAGE FORM FOR DELIVERING DRUG AT A CONTROLLED RATE TO THE INTESTINE AND TO THE COLON

[75] Inventors: Jeremy Corwin Wright, Los Altos; George V. Guittard, Cupertino, both of Calif.

[73] Assignee: Alza Corporation, Palo Alto, Calif.

[21] Appl. No.: 696,473

[22] Filed: May 6, 1991

Related U.S. Application Data

[62] Division of Ser. No. 498,121, Mar. 23, 1990, Pat. No. 5,178,866.
[51] Int. Cl.⁶ ........................................................ A61K 9/24
[52] U.S. Cl. ...................... 424/473; 424/467; 424/468; 604/892.1
[58] Field of Search .................... 424/473, 423, 424/424, 438, 467, 468, 466; 604/892.1

[56] References Cited

U.S. PATENT DOCUMENTS

| | | |
|---|---|---|
| 3,845,770 | 11/1974 | Theeuwes et al. .................. 128/260 |
| 4,036,227 | 7/1977 | Zaffaroni et al. .................. 128/260 |
| 4,503,030 | 3/1985 | Edgren et al. ..................... 424/473 |
| 4,627,851 | 12/1986 | Wong et al. ........................ 424/467 |
| 4,717,566 | 1/1988 | Eckenhoff et al. ................. 424/438 |
| 4,855,141 | 8/1989 | Eckenhoff et al. ................. 424/423 |
| 4,904,473 | 2/1990 | Theeuwes et al. .................. 424/424 |
| 4,904,474 | 2/1990 | Theeuwes et al. .................. 424/424 |
| 5,004,614 | 4/1991 | Staniforth ........................ 424/466 |

*Primary Examiner*—John C. Bleutge
*Assistant Examiner*—Robert H. Harrison
*Attorney, Agent, or Firm*—Paul L. Sabatine; Mary Ann Dillahunty; Felissa H. Cagan

[57] ABSTRACT

A drug delivery device is disclosed for delivering a drug to the intestine and the colon. The device comprises external means for delaying the delivery of drug in the stomach, and hydrophobic means for preventing the passage of fluid through the delay means.

5 Claims, 2 Drawing Sheets

DOSAGE FORM FOR DELIVERING DRUG AT A CONTROLLED RATE TO THE INTESTINE AND TO THE COLON

CROSS-REFERENCE TO RELATED APPLICATIONS

This application is a division of Ser. No. 07/498,121, filed on Mar. 23, 1990, now U.S. Pat. No. 5,178,866, which is incorporated herein by reference, and benefit is claimed of its filing date.

DISCLOSURE OF TECHNICAL FIELD

The present invention pertains to a novel delivery system for administering a therapeutic drug to a preselected region of the gastrointestinal tract, specifically the intestine. The invention concerns also a method for administering orally a drug to the intestine of a warm-blooded animal.

DISCLOSURE OF THE BACKGROUND ART

As is known in the medical and the pharmaceutical arts, the desiderata of an enteric coat is to protect an orally administered drug from the environment of the stomach. The enteric coat provides protection from the environment of the stomach including its fluids, its acidity, its enzymes and peristaltic agitation in the stomach. It is desirable also for the enteric coat to maintain its integrity during the time needed for the drug to pass through the stomach and enter the intestine.

Heretobefore, enteric coats were used to safeguard a drug in the stomach, but frequently they were not satisfactory. One reason they were not satisfactory is they allowed water transport through the enteric coat causing the drug to be released prematurely. For some dosage forms, such as an osmotic device, the passage of water through the enteric coat hydrates the device and this causes the drug to be released too rapidly and early once the device enters the intestine and the enteric coat disintegrates. Consequently, as a result of this action, the drug may be absorbed or metabolized at the start of the intestine and it is not delivered at a controlled rate throughout the intestine for its intended effect. One effort to overcome this consists in applying thicker enteric coats, however, this too lets fluid flux therethrough and the thicker coats often rupture under the influence of agitation in the stomach.

In view of the above presentation, it is immediately self-evident that a need exists for a dosage form comprising an enteric coat that comprises means for substantially preventing the passage of water through its enteric coat. The need exists for a dosage form comprising an enteric coat that is hydrophobic for preventing the flux of water through the enteric coat particularly during the time the dosage form is in the stomach.

DISCLOSURE OF OBJECTS OF THE INVENTION

It is an immediate object of this invention to provide a novel dosage form comprising an enteric coat that overcomes the aforesaid disadvantages associated with the prior art dosage forms.

It is another object of this invention to provide a dosage form manufactured as an osmotic device comprising an enteric coat that substantially prevents the passage of water therethrough.

It is another object of this invention to provide an osmotic device for the controlled delivery of a beneficial drug to the intestine, which delivery device represents an advancement in intestine-specific therapy.

It is another object of this invention to provide a dosage form that provides intestine and colon specific therapies.

It is another object of this invention to provide an osmotic device that delays the onset of drug release from the osmotic device for a period of time required for the osmotic device to pass through the stomach and enter the small intestine.

It is another object of this invention to provide an osmotic device comprising an enteric coat that comprises hydrophobic means for preventing the passage of biological fluid including water through the enteric coat.

It is yet another object of this invention to provide an osmotic device comprising an exterior enteric coat comprising a hydrophobic composition that impedes fluid transport into the osmotic system until the interior semipermeable wall of the device is exposed to fluid.

It is another object of this invention to provide an osmotic device comprising a semipermeable wall carrying on its outer surface means for delaying the delivery of a drug during the time required for the osmotic device to pass through the stomach.

It is another object of this invention to provide an osmotic device that delivers a drug to a preselected area of the gastrointestinal tract, comprising the intestine and the colon.

It is yet another object of this invention to provide an osmotic device comprising a wall carrying an exterior enteric composition comprising at least two components for restricting the passage of a biological fluid through the intact composition.

It is another object of this invention to provide an osmotic device comprising means for denying fluid access to the device and for concomitantly denying fluid imbibition into the device.

Other objects, features, aspects and advantages of this invention will be more apparent to those versed in the dispensing art from the following detailed specification taken in conjunction with the drawing figures and the accompanying claims.

BRIEF DISCLOSURE OF THE DRAWINGS

In the drawing figures, which are not drawn to scale, but are set forth to illustrate various embodiments of the invention, the drawing figures are as follows:

FIG. 2, is a view of the dosage form of FIG. 1, wherein FIG. 2 depicts an exterior coat for substantially preventing fluid passage into the dosage form;

FIG. 3, is an opened view of the dosage form of FIG. 1 and FIG. 2, wherein FIG. 3 depicts the structure of the dosage form;

In the drawing figures and in the specification, like parts in related drawing figures are identified by like numbers. The terms appearing earlier in the specification and in the description of the drawing figures, as well as embodiments thereof, are further detailed elsewhere in the specification.

DETAILED DISCLOSURE OF THE DRAWING FIGURES

Figure 1:
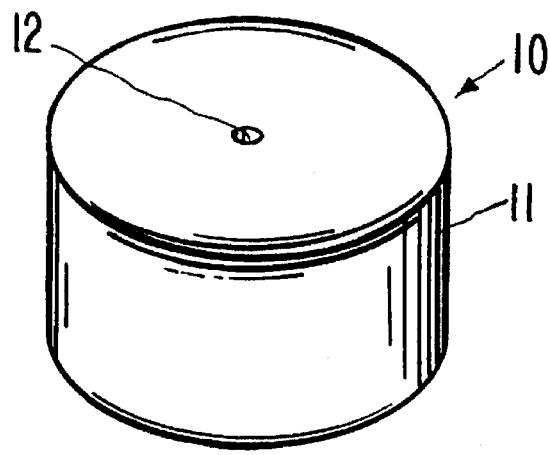
FIG. 1, is a view of a dosage form designed for administering orally a therapeutic drug to the gastrointestinal tract regions comprising the intestine and colon regions.

Turning now to the drawing figures in detail, which drawings are examples of the delivery systems provided by the invention and are preferably manufactured as osmotic devices, and which examples are not to be construed as limiting, one example of an osmotic device as seen in FIG. 1, identified by the numeral 10. In FIG. 1, the osmotic device 10 is sized, shaped and adapted for use as an orally administrable osmotic dosage form. The osmotic device 10 comprises a body 11 and a passageway 12, for connecting the exterior with the interior of osmotic device 10, not seen in FIG. 1.

Figure 2:
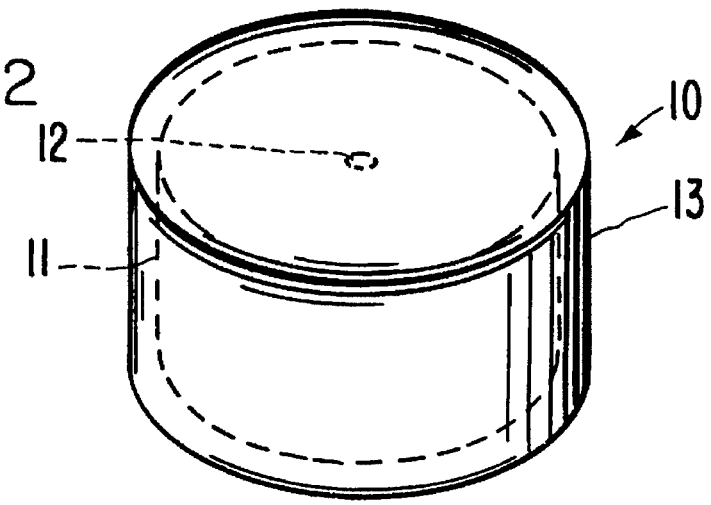

Drawing FIG. 2 depicts osmotic device 10 comprising an exterior coat 13. Exterior coat 13 is an enteric coat designed for simultaneously (a) preventing osmotic device 10 from delivering a drug in the stomach, and (b) preventing fluids such as biological fluids and water from entering osmotic device 10.

Figure 3:
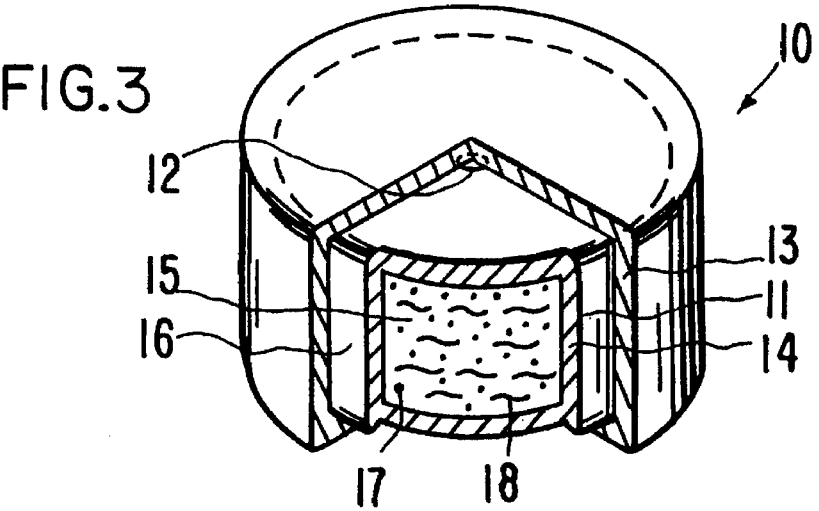

Drawing FIG. 3 depicts osmotic device 10 in opened view for illustrating the structural members of osmotic device 10. In FIG. 3, device 10 comprises body 11 and wall 14. Wall 14 comprises at least one passageway 12 that extends through wall 14 for connecting the exterior of device 10 with an interior compartment 15. Wall 14 comprises in total, or at least in part a semipermeable composition that is permeable to the passage of an external fluid present in the environment of use, such as biological fluids, aqueous and aqueous-like fluids. Wall 14 is essentially impermeable to the passage of drug. Wall 14 is substantially inert, and it keeps its physical and chemical integrity during the dispensing-life of a drug. Wall 14 comprises a composition that is non-toxic to animals, including humans.

In drawing FIG. 3, dosage form 10 comprises an exterior coat 13 for (a) essentially delaying the delivery of a drug from dosage form 10 during the passage of dosage form 10 through the stomach; for (b) essentially preventing the passage of biological and aqueous fluid through coat 13; and, for (c) essentially preventing exterior biological and aqueous fluids from contacting the exterior surface 16 of wall 14. The exterior surface 16 of wall 14 faces the environment of use, that is, the gastrointestinal tract.

Exterior coat 13 comprises a composition that maintains its physical and chemical integrity in an acid environment such as the stomach, and it maintains its physical and chemical integrity in the presence of agitation in the stomach. The phrase, maintains its physical and chemical integrity, as used for the purpose of this invention means coat 13 does not dissolve, disintegrate, or break-up in the stomach. Coat 13 consequently as carried on wall 14 delays the release of drug from dosage from 10 during coat 13 tenure on the exterior surface 16 of wall 14. The word hydrophobic as used herein denotes substantially a lack of affinity for water and substantially impermeable to the passage of water, biological fluids, and lipophilic fluids.

Compartment 15, in one preferred embodiment, comprises a therapeutic drug 17, represented by dots. Drug 17 can be soluble to very soluble in an external fluid imbibed into compartment 15, and it exhibits an osmotic pressure gradient across wall 14. Compartment 15, in another embodiment, comprises drug 17 that is insoluble to poorly soluble in the external fluid, and in this instance drug 17 exhibits a limited osmotic pressure gradient across wall 14. In this latter embodiment, drug 17 optionally is mixed with an osmagent 18, indicated by wavy lines, that is soluble in the external fluid and it exhibits an osmotic pressure gradient across wall 14 against an external fluid.

Figure 4:
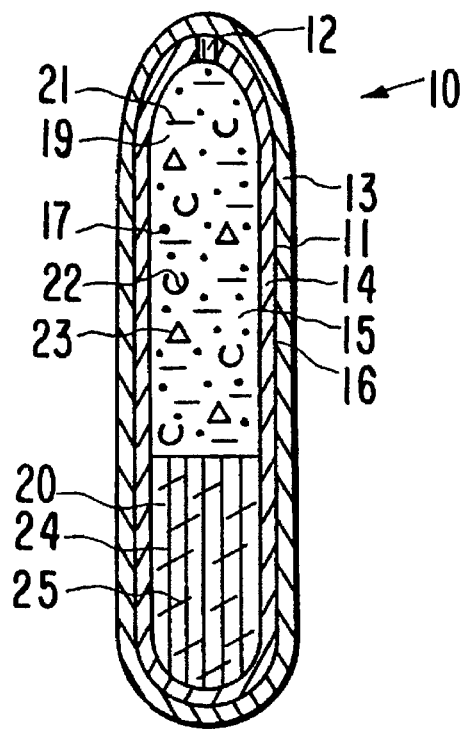
FIG. 4, is a view of the dosage form provided by this invention manufactured as a different embodiment for administering a therapeutic drug to the preselected intestine and colon areas of the gastrointestinal tract; and, FIG. 5 is a graph that depicts the release rate from a delivery device first in artificial gastric fluid, and then in artificial intestinal fluid.

Drawing FIG. 4 illustrates another embodiment of dosage form 10. In drawing FIG. 4, dosage form 10 comprises internal wall 14 that surrounds internal compartment 15. Passageway means 12 through internal wall 14 connects the exterior of dosage form 10 with compartment 15. An exterior coat 13 prevents dosage form 10 from delivering a drug in the stomach and it concomitantly prevents fluid from passing through wall 14. Coat 13, in its initial embodiment seals passageway 12 until coat 13 is released from dosage form 10. In drawing FIG. 4, internal compartment 14 comprises a first composition 19 and a second composition 20. First composition 19 comprises a therapeutically active drug 17 that can be from insoluble to very soluble in fluid imbibed into the compartment. Drug 17 optionally is mixed with an osmagent 21, represented by dashes, that is soluble in fluid imbibed into compartment 14 and exhibits an osmotic pressure gradient across semipermeable wall 14 against an external fluid. First composition 19 in another preferred embodiment, comprises an osmopolymer 22, represented by half-circles, that imbibes fluid into the first composition 19 to form a dispensable drug formulation. First composition 19 optionally comprises other therapeutic composition forming ingredients 23, represented by triangles, such as lubricants, binders, and the like. First composition 19 is non-toxic and it comprises pharmaceutically acceptable ingredients.

Second composition 20 is in contacting relation with first composition 19. Second composition 20 is an osmotic driving force that expands and pushes dispensable first composition 19 from device 10. The second composition in operation imbibes fluid into the second composition, absorbs the imbibed fluid into the second composition, and expands in compartment 15. The continuous uptake of incoming fluid by composition 20 causes it to continuously expand and push first composition 19 through passageway 12 into the preselected area of the gastrointestinal tract. In one presently preferred embodiment, second composition 22 comprises an osmopolymer 24, also known as a hydrophilic hydrogel, that exhibits an osmotic pressure gradient across wall 14 against an external fluid present in the gastrointestinal tract. In another presently preferred embodiment, second composition 20 comprises an osmopolymer 24 and an osmagent 25, depicted by slant dashes. Osmagents are known also as osmotically effective compounds, and as osmotic solutes, and they exhibit an osmotic pressure gradient across a semipermeable wall 14 against a fluid present in the animal environment of use. The osmopolymer in cooperation with the osmagent imbibe fluid into second composition 20 for optimizing the maximum expansion of second composition 20 to an enlarged state for pushing dispensable composition 19 through drug releasing exit means 12 from device 10.

Delivery system 10, as seen in FIGS. 1 to 4 can be made into many embodiments for oral use for administering a locally or a systemically acting therapeutically acting drug in the intestine, or in the intestine and colon of the gastrointestinal tract. In one presently preferred embodiment, the delivery device for oral use can have various conventional shapes and sizes such as round, egg-shape, kidney-bean shape, and the like. The oral delivery system can comprise a small to a large diameter, such a 5/16 inches to 9/16 inches, and the like. The oral dosage systems in another manufacture are optionally sized and shaped as small tiny osmotic pills having a diameter of about 2 mm to 10 mm. The small dosage systems can be administered individually or as a plurality of tiny pills in a single piece or a two piece capsules. The capsule can house 1, 5 or a plurality of small dosage pills from 1 to 100, or the like.

DETAILED DISCLOSURE OF THE INVENTION

In accordance with the practice of this invention, wall 14 comprises a composition that is permeable to the passage of fluid, and is substantially impermeable to the passage of drugs, osmotic solutes, binders, suspending agents and the like. The semipermeable composition does not adversely affect the active drug, nor an animal host. The selectively permeable materials comprising wall 14 are semipermeable materials that are insoluble in body fluids and they are non-erodible. Representative selective materials for forming wall 14 comprise semipermeable polymer, homopolymer, copolymers and the like. The polymeric compositions presently preferred for manufacturing wall 14 comprise a member selected from the group consisting of cellulose acylate, cellulose diacylate, cellulose triacylate, cellulose ester, cellulose ether, and cellulose ester-ether. Exemplary semipermeable polymers comprise cellulose acetate, cellulose diacetate, cellulose triacetate, dimethylcellulose acetate, cellulose acetate propionate, cellulose acetate butyrate, and the like. Semipermeable polymers are known in U.S. Pat. Nos. 3,173,876; 3,276,586; 3,541,005; 3,541,006; 3,546,142; 3,845,770; 3,916,899; 4,036,228; and 4,111,202.

Exterior, enteric coat 13 that substantially prevents delivery device 10 from releasing a drug in the stomach and simultaneously substantially prevents passage of fluid through coat 13, comprises a composition that does not dissolve, disintegrate, or change its structural nature in the stomach and during the period of time delivery device 10 needs to pass through the stomach. The exterior coat 13 provided by this invention comprises at least one compounds, that forms the exterior, enteric coat, and at least one hydrophobic compound that substantially prevents fluid flux therethrough. Representative composition that keep their integrity in the stomach comprise a member selected from the group consisting of (a) keratin, keratin sandaractolu, salol, salol beta-naphyl benzoate and acetotannin, salol with balsam of Peru, salol with tolu, salol with gum mastic, salol and stearic acid, and salol and shellac; (b) a member selected from the group consisting of formalized protein, formalized gelatin, and formalized cross-linked gelatin and exchange resins; (c) a member selected from the group consisting of myristic acid-hydrogenated castor oil-cholesterol, stearic acid-mutton tallow, stearic acid-balsam of tolu, and stearic acid-castor oil; (d) a member selected from the group consisting of shellac, ammoniated shellac, ammoniated shellac-salol, shellac-wool fat, shellac-acetyl alcohol, shellac-stearic acid-balsam of tolu, and shellac n-butyl stearate; (e) a member selected from the group consisting of abietic acid, methyl abietate, benzoin, balsam of tolu, sandarac, mastic with tolu, and mastic with tolu, and mastic with acetyl alcohol; (f) acrylic resins represented by anionic polymers synthesized from methacrylic acid and methacrylic acid methyl ester, copolymeric acrylic resins of methacrylic and methacrylic acid and methacrylic acid alkyl esters, copolymers of alkacrylic acid and alkacrylic acid alkyl esters, acrylic resins such as dimethylaminoethylmethacrylate-butylmethacrylate-methylmethacrylate copolymer of 150,000 molecular weight, methacrylic acid-methylmethacrylate 50:50 copolymer of 135,000 molecular weight, methacrylic acid-methylmethacrylate-30:70-copolymer of 135,000 mol. wt., trimethylammoniumethyl-methacrylatechloride-methylmethacrylate-ethylacrylate-10:60:30 copolymers of 135,000 mol. wt., trimethylammoniumethyl-methacrylate-chloride-methylmethacrylate-ethylacrylate-5:65:30-copolymer of 150,000 mol. wt., ethylacrylate-methylmethacrylate-70:30-copolymer of 800,000 mol. wt., methacrylic acid-ethylacrylate-50:50-copolymer of 250,000 mol. wt., methacrylic acid-dimethylaminoethyl-methacrylate-ethylacrylate of 750,000 mol. wt., methacrylic acid-methylmethacrylate-ethylacrylate of 1,000,000 mol. wt., and ethylacrylate-methylmethacrylate-ethylacrylate of 550,000 mol. wt; and, (g) an enteric composition comprising a member selected from the group consisting of cellulose acetyl phthalate, cellulose diacetyl phthalate, cellulose triacetyl phthalate, cellulose acetate phthalate, hydroxypropyl methylcellulose phthalate, sodium cellulose acetate phthalate, cellulose ester phthalate, cellulose ether phthalate, methylcellulose phthalate, cellulose ester-ether phthalate, hydroxypropyl cellulose phthalate, alkali salts of cellulose acetate phthalate, alkaline earth salts of cellulose acetate phthalate, calcium salt of cellulose acetate phthalate, ammonium salt of hydroxypropyl methylcellulose phthalate, cellulose acetate hexahydrophthalate, hydroxypropyl methylcellulose hexahydrophthalate, polyvinyl acetate phthalate diethyl phthalate, dibutyl phthalate, dialkyl phthalate wherein the alkyl comprises from 1 to 7 straight and branched alkyl groups, aryl phthalates, and the like.

The hydrophobic compound homogenously blended with the enteric coat exemplified by groups (a) through (g) comprises a homogenous compound from the same group or a hydrophobic compound from a different group. The hydrophobic compound homogenously blended with an enteric coat represented by groups (a) through (g) in a presently preferred embodiment comprises a member selected from the group consisting of cellulose acetyl phthalate, cellulose diacetyl phthalate, cellulose triacetyl phthalate, cellulose acetate phthalate, hydroxypropyl methylcellulose phthalate, sodium cellulose acetate phthalate, cellulose ester phthalate, cellulose ether phthalate, methylcellulose phthalate, cellulose ester-ether phthalate, hydroxypropyl cellulose phthalate, alkali salts of cellulose acetate phthalate, alkaline earth salts of cellulose acetate phthalate, calcium salt of cellulose acetate phthalate, ammonium salt of hydroxypropyl methylcellulose phthalate, cellulose acetate hexahydrophthalate, hydroxypropyl methylcellulose hexahydrophthalate, polyvinyl acetate phthalate diethyl phthalate, dibutyl phthalate, dialkyl phthalate wherein the alkyl comprises from 1 to 7 straight and branched alkyl groups, aryl phthalates, and the like.

In a presently preferred embodiment the hydrophobic compound is blended into the enteric coat in excess of solubility in the enteric coat. The hydrophobic compound in the enteric coat migrates to the surfaces of the enteric coat wherein it impedes fluid transport into delivery system 10. In this manufacture, the invention provides an improvement over standard enteric coats which while not disintegrating let fluid pass at pH of the stomach. This invention provides a hydrophobic compound in the enteric coat for substantially preventing fluid transport through the enteric coat. The hydrophobic compounds, in one presently preferred embodiment are mixed initially with the entire coat in a pharmaceutically acceptable form selected from the group consisting of crystalline, particle, pellet, granule, powder, dry and lyophilized forms. In this embodiment the added hydrophobic compounds can homogeneously or heterogeneously blend with the entire coat and they are presently available for migrating to the surface of the entire coat. The amount of hydrophobic compound in the exterior, enteric coat about 1 weight percent to 50 weight percent, and in a presently more preferred amount by 10 weight percent to 50 weight percent. The enteric percent to 50 weight percent. The enteric compounds are known in *Remington's Pharmaceutical Sciences*, 13th Ed., pages 604–605, (1965), published by Mack Publishing Co., Eaton, Pa.; Eudragit® Coatings Rohm Pharma., (1985); and U.S. Pat. No. 4,627,851.

The term, drug 17, as used for the purpose of this invention embraces drug that are administered in the lower gastrointestinal to produce a therapeutic effect. The drugs include the drugs conventionally used in the treatment of colitis, ulcerative colitis, Crohn's disease, idiopathic prototis and other diseases of the lower gastrointestinal tract. Representative drugs include salicylazosulfapyridine, also known as sulphasalazine, and salazopyrin; adrenocorticosteroids such as hydrocortisone, prednisolone, prednisolone phosphate, prednisolone sulfate, prednisone, prednisolone, prednisolone metasulpho-benzoate sodium, prednisolone sodium phosphate and the like; corticosteroids such as beclomethasone, beclomethasone acetate, beclomethasone valerate, beclomethasone propionate, beclomethasone dipropionate, and the like; cyclosporin; and the like. In another aspect, drug 17 also includes drugs for treatment of irritable bowel syndrome, or drug 17 alters bowl motility and fluid absorption, such drugs are represented by calcium channel blocking drugs, opiads, anticholinergics and benzodiazepides. The amount of drug in a delivery device 10 can be from 10 ng to 1.5 g, and the amount of drug in the tiny dosage forms is from 10 ng, to 25 mg, and the like.

The osmotically effective compounds that can be used for the purpose of this invention for mixing with a drug, or for mixing with an osmopolymer comprise inorganic and organic compounds that exhibit an osmotic pressure gradient across a semipermeable against an external fluid. The osmotically effective compounds imbibe fluid into the device thereby making available in situ fluid for imbibition by an osmopolymer to enhance its expansion, or for forming a solution or suspension comprising a drug for its delivery through a passageway from the delivery system. Osmotically effective compounds are known also as osmotically effective solutes or osmagents and they are exemplified by magnesium sulfate, magnesium chloride, potassium sulfate, sodium sulfate, lithium sulfate, sodium chloride, potassium acid phosphate, mannitol, glucose, urea, inositol, magnesium succinate, potassium chloride, tartaric acid, carbohydrates such as raffinose, succrose, alpha-d-lactose monohydrate, and mixtures thereof. The amount of osmagent mixed with a drug generally is from 0.01% to 30%, or higher, and the amount of osmagent when mixed with an osmopolymer is from 0.01% to 40%, or higher. Osmagents are known in U.S. Pat. No. 4,765,989.

The first composition 19, as seen in FIG. 4, comprises a non-toxic polymer that forms a drug disposable formulation comprising for example a hydrophilic polymer that exhibits the ability to absorb or imbibe fluid and retain the fluid to form a viscous solution, or the like. In a presently preferred embodiment, the hydrophilic polymer is a drug carrier means, usually a noncross-linked hydrogel and it is preferably a different hydrogel than the expandable hydrogel comprising second composition 20. Generally, the hydrogel for carrying the drug will have a viscosity of about 100 centipoise at a 5% concentration to a solution viscosity of 1000 centipoise at a similar concentration. The solution viscosity of a polymer can be measured using a Brookfield viscometer. Methods for measuring viscosity are disclosed in *Pharmaceutical Sciences*, by Remington, 14th Ed., pp 361–371, (1970), published by Mack Publishing Co., Easton, Pa. Methods for measuring viscosity are disclosed in *Encyclopedia of Chemists*, by Clark, 2nd Ed., pp 663–667, (1966), published by Van Nostrand Reinhold Co., New York; and in *Handbook of Common Polymers*, by Scot, Sect. 52, pp 487–493, (1971), published by Chemical Rubber Co., Cleveland, Ohio.

In FIG. 4, first composition 19, in one presently preferred embodiment comprises a water soluble, nonionic hydrophilic polymer, such as from 75 weight percent to 95 weight percent of a polyethylene oxide selected from the group consisting of a polyethylene oxide having a 100,000 molecular weight, a polyethylene oxide having a 200,000 molecular weight, a polyethylene oxide having a 300,000 molecular weight, and the like; from 0 weight percent to 20 weight percent of a hydroxypropylmethylcellulose having a 9,000 to 20,000 number average molecular weight. The first composition optionally comprises from zero weight percent to 3 weight percent of lubricant such as stearic acid, or magnesium stearate, and from 0 weight percent to 10 weight percent of a binder such as polyvinyl pyrrolidone, with the total weight percent of all ingredients equal to 100 weight percent.

Second composition 20, in FIG. 4, comprises means for interacting with aqueous and biological fluid, for swelling or expanding for pushing the first composition 19 from the delivery device. The second composition 20 comprises means for retaining a significant portion of imbibed and absorbed fluid within its molecular structure. Representative compositions comprise osmopolymers that are noncross-linked or lightly cross-linked by covalent or ionic bonds. The osmopolymers can be of natural or of synthetic origin. The osmopolymers are hydrophilic polymers. Representative polymers for forming second composition 17 include poly(hydroxyalkylmethacrylate) having a molecular weight of from 30,000 to 5,000,000; poly(vinylpyrrolidone) having a molecular weight of from 10,000 to 360,000; anionic and cationic hydrogels; polyelectrolyte complexes; poly(vinyl alcohol) cross-linked with glyoxal, formaldehyde or glutaraldehyde and a degree of polymerization from 20,000 to 30,000; a mixture of cross-linked agar, methyl cellulose and carboxymethyl cellulose; a water insoluble, water swellable copolymer reduced by forming a dispersion of finely divided copolymer of maleic anhydride with styrene, ethylene, propylene, butylene or isobutylene cross-linked with from 0.001 to about 0.5 moles of polyunsaturated cross-linking agent per mole of maleic anhydride in the copolymer; water swellable polymers of N-vinyl lactams; and the like.

In another presently preferred embodiment, second composition 20 comprises a member selected from the group consisting of acidic carboxy polymers having a molecular weight of 450,000 to 4,000,000; polyacrylamides; cross-linked water swellable indene-maleic anhydride polymers; polyacrylic acid having a molecular weight of 80,000 to 200,000; polyalkylene oxide polymers having a molecular weight of 100,000 to 8,000,000; starch graft copolymers; acrylate polymers; diester cross-linked polyglucan; and the like. Representative polymers that form hydrogels are known to the prior art in U.S. Pat. No. 3,865,108 issued to Hartop; U.S. Pat. No. 4,002,173 issued to Manning; U.S. Pat. No. 4,207,893 issued to Michaels, and in *Handbook of Common Polymers*, by Scott and Roff, published by Chemical Rubber Company, Cleveland, Ohio.

The expression, exit means, as used herein, comprises means and methods suitable for the metered release of beneficial drug of dosage from the internal compartment of dosage form 10. The exit means include at least one passageway, orifice or the like, through wall for communicating with compartment. The expression, at least one passageway, includes aperture, orifice, bore, pore, porous element through which the drug can migrate, hollow fiber, capillary tube, porous overlay, porous insert, and the like. The expression also includes a material that erodes or is leached from wall in the fluid environment of use to produce at least one passageway in dosage form 10. Representative materials suitable for forming at least one passageway, or a multiplicity of passageways, include an erodible poly (glycolic) acid or erodible poly(lactic) acid member in the wall; a gelatinous filament; poly(vinyl alcohol); leachable materials such as fluid removable pore forming polysaccharides; salts, oxides, and the like. A passageway or a plurality of passageways can be formed by leaching a material such as sorbitol, lactose, or the like, from the wall. The passageway can have any shape such as round, triangular, square, elliptical, and the like, for assisting in the metered release of drug from dosage form. Dosage form can be constructed with one or more passageways in spaced apart relations, or more than one passageway on a single surface of dosage form. Passageways and equipment for forming passageways are disclosed in U.S. Pat. Nos. 3,845,770; 3,916,899; 4,063,064; and 4,088,864. Passageways for releasing a drug formed by leaching or controlled pore forming are disclosed in U.S. Pat. No. 4,200,098 and 4,285,987.

The wall of a dosage form, and the exterior coat can be formed in separate steps using the air suspension procedure. This procedure consists in suspending and in tumbling the drug forming compartment in a current of air and then coating with a wall forming composition, or followed by the exterior coat composition until, in either operation the wall or the exterior coat is applied to the layered drug forming compartment. The air suspension procedure is well-suited for independently forming the wall on the enteric coat. The air suspension procedure is described in U.S. Pat. No. 2,799,241; in *J. Am. Pharm. Assoc.* Vol. 48, pp 451–59, (1959); and ibid., Vol. 49, pp 82–4, (1960). Dosage-forming devices can also be coated with the wall forming composition or with the enteric forming composition, with a Wurster® air suspension coater using various solvents such as methylene dichloride-methanol cosolvent 80/20 (w/w), using 2.5 to 4% solids. The Aeromatic® air suspension coater using a methylene dichloride/methanol cosolvent 87/13 (w/w) also can be used for applying the wall, or the enteric coat. Other wall and delayed coating techniques such as pan coating can be used for providing the delivery device. In the pan coating system, wall forming, or enteric coating compositions are deposited by successive spraying of the compositions of the compartment forming cores, accompanied by tumbling in a rotating pan. A pan coater also is used to produce a thicker wall or a thicker enteric coat. A larger volume of solvent can be used in a cosolvent to produce a thinner wall or an enteric coat. Finally, the wall with the exterior coated compartment are dried in a forced air oven at 50° C. for a week to free the dosage form of solvent. Generally, the wall formed by these techniques will have a thickness of 2 to 20 mils with a presently preferred thickness of 4 to 10 mils. The exterior coat generally will have a thickness of 0.5 to 15 mils, usually 0.5 to 7.5 mils.

Exemplary solvents suitable for manufacturing the wall or the exterior coat include inorganic and organic solvents that do not adversely harm the wall, the outer coat nor the final delivery system. The solvents broadly include a member selected from the group consisting of alcohol, ketone, ester, ether, aliphatic hydrocarbons, halogenated solvents, cycloaliphatic solvents, aromatic, heterocyclic, aqueous solvents, and mixtures thereof.

The dosage form as seen in FIG. 3 can be made by a dry granulation process of manufacture. The dry process comprises first mixing all the composition forming ingredients, except for the lubricant, passing the mixed ingredients through a grinding mill to a small mesh size, and then transferring the sized powder to a dry compactor. The compactor densifies the powder and is extruded as a sheet or ribbon which is then passed through a sizing mill to regrind the composition. The composition is ground to a small size, typically 20 mesh or smaller. Finally, a dry lubricant is added and the ingredients blended to produce the final composition. Then, the respective composition is fed to a bi-layer tablet press and each composition is intimately bonded into contacting layers comprising dosage form 10.

In another manufacturing, the dosage form is manufactured by the wet granulation technique. In the wet granulation technique, the drug and the ingredients are blended using an organic solvent. First, the ingredients are individually passed dry through a mesh screen and then thoroughly blended in a mixer. Next, other ingredients are dissolved in a portion of the granulation fluid and this latter prepared granulating solution is added slowly to the drug blend with continual mixing in the blender. The granulating fluid is added until a wet blend is produced, which wet mass then is forced through a 20 mesh screen onto oven trays. The blend is dried for 18 to 24 hours at 50° C. The dry granules are then sized using a 20 mesh screen. Next, a lubricant is passed through a screen and added to the dry granule blend. The granulation is placed into a blender and mixed for 5 to 10 minutes. The composition is then compressed into drug cores and coated with the inside semipermeable membrane wall and the exterior coat.

First composition 19 and second composition 20 are manufactured from well mixed individual composition forming members. For example a first composition is made as follows: first, each of the ingredients comprising a dosage form is independently screened and then blended together, except for a lubricant. Then, the homogeneous blend is wet granulated by adding a solvent such as anhydrous ethanol, and the wet ingredients mixed until a uniform blend is obtained by said process. Next, the wet blend is passed through a screen and dried to evaporate the solvent. The resulting granules are passed again through a sieve. Next, a small amount of a finely divided lubricant is added to the dry granules and the lubricant and granules blended to provide a uniform blend. Then, the first composition is fed to a hopper of a bilayer tablet press, and the first composition pressed into the first layered composition. The process is repeated for the second composition. Typically about one-fourth to two tons of pressure are applied to yield the dosage form, which is coated with the internal semipermeable membrane wall and then the exterior coat.

The following examples are merely illustrative of the present invention, and it should not be considered as limiting the scope of the invention in any way, as this example and other equivalents thereof will become apparent to those versed in the drug delivery art in light of the present disclosure and the accompanying claims.

DISCLOSURE OF EXAMPLES FOR PROVIDING THE INVENTION

EXAMPLE 1

A delivery device for administering a therapeutic drug to the intestine and colon of a warm-blooded animal is made as follows: first, in a standard blender, 1,000 g of hydroxypropylmethylcellulose having a 9,600 molecular weight is blended with 18,114 g of polyethylene oxide having a 300,000 molecular weight, to yield a uniform mass. Next, 800 g of polyvinylpyrrolidone is dissolved in 6 liters of anhydrous, ethyl alcohol with stirring, and when all the polyvinylpyrrolidone is in solution, 86 g beclomethasone dipropionate is added to solution, with constant stirring to yield a granulation solution. Then, the granulation solution is added slowly to the hydroxypropylmethylcellulose, polyethylene oxide blend and the alcohol content raised to 10 liters. Then, the wet mass is mixed for 10 minutes in a blender. Next, the wet mass is passed through an 8 mesh screen to form wet granules. The wet granules are dried in a forced air circulating oven overnight at 25° C. Finally, the oven temperature is raised to 50° C. and drying continued for 2 hours to remove the last traces of ethyl alcohol. Finally, the dry granules are passed through a 20 mesh stainless steel screen and stored in a closed container.

Next, a second composition is prepared as follows: first, 9,705 g of polyethylene oxide having a 5,000,000 molecular weight, 4,395 g of sodium chloride, 750 g of hydroxypropylmethylcellulose and 150 g of red ferric oxide are blended to produce a homogenous blend, and the blend passed through a 40 mesh stainless steel screen. The screened particles are next blended with granulating fluid comprising anhydrous ethanol to produce a wet blend. The total volume of granulating fluid used is about 8 liters. The wet mass is passed through a 15 mesh sizing screen to form wet granules. The wet granules are transferred to drying sheets and dried in a forced air circulating oven at 25° C. over 16 to 24 hours to remove the granulating fluid, ethyl alcohol. The dry granules are stored in a closed containers until needed for further formulation of the delivery device.

Next, the first composition and the second composition are pressed into a first layer and a second layer in a tabletting machine. The first composition is laminated against the second composition to provide a drug-push core. The first composition comprises 0.4348 wt % of beclomethasone dipropionate, 5.0 wt % of hydroxypropylmethylcellulose, 90.57 wt % of polyethylene oxide and 4.0 wt % of polyvinylpyrrolidone. The second composition comprises 64.70 g wt % of polyethylene oxide, 29.30 wt % of sodium chloride, 5.0 wt % of hydroxypropylmethylcellulose and 1.0 wt % red ferric oxide.

Next, a semipermeable wall is applied around the contacting laminated compositions. The wall forming composition comprises 97 wt cellulose triacetate having an acetyl content of 43.5% and 3 wt % polyethylene glycol 3350. The wall forming solvent comprises 80 parts of methylene chloride and 20 parts of methanol, wt/wt. The wall forming composition comprises 3% solids. The wall forming ingredients are dissolved in the solvents and stirred until a clear solution is obtained. The wall is formed in an Accela-Cota® pan coater to an approximate thickness of 0.076 mm (3 mils). After drying, and removing the cosolvent, a 0.25 mil orifice is laser drilled in the semipermeable wall to communicate with the first, drug layer. The drilled systems are placed on opened trays in a humidity oven set at 50% relative humidity at 50° C. for 24 hours to remove the remaining solvent.

Next, an exterior coat is prepared in a blender containing 95 part ethyl alcohol and 5 parts of distilled water, wt/wt, to which is added slowly and with constant stirring 90 g of copolymeric methacrylic acid-methylmethacrylate, to produce a clear solution. Then, 10 g of hydrophobic dibutyl phthalate is added to the blender and stirring continued for 30 minutes. The final concentration of the exterior coat comprises 90% copolymer and 10% hydrophobic compound to give a 3% solids exterior coat.

Next, the semipermeable wall coated delivery systems are placed into an air suspension coater and the exterior coating composition is added to the coater, and the delivery systems uniformly coated with an exterior coat. The exterior coated delivery systems are removed from the coater, placed on trays, and dried in a forced air circulating oven at 50° C. for 24 hours to yield the final delivery system.

EXAMPLE 2

Figure 5:
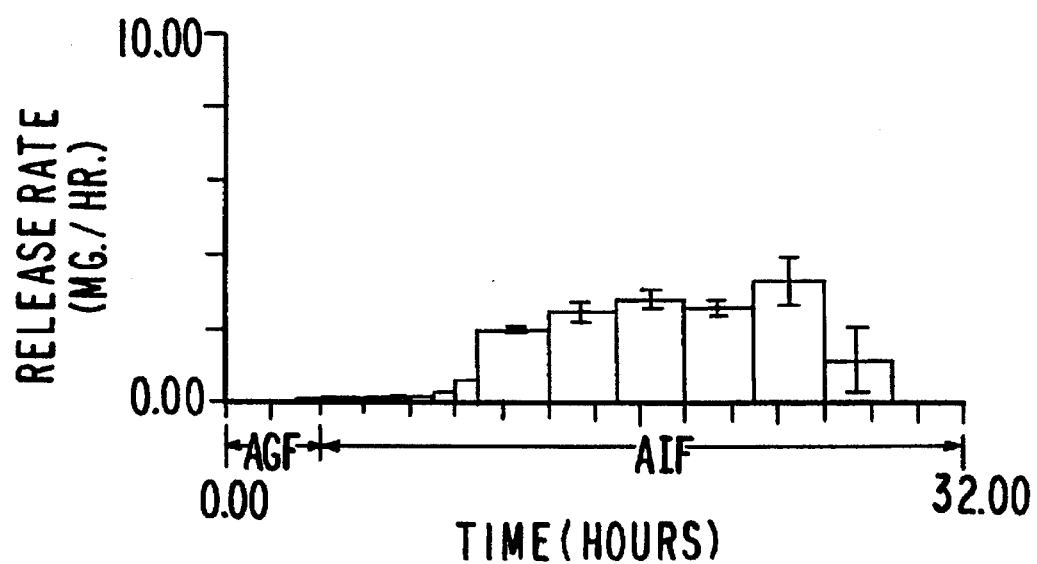

The procedure of Example 1 is repeated with all the steps as set forth, except that in this example the exterior coat comprises 75 wt % methacrylic acid-methylmethacrylate copolymer and 25 wt % hydrophobic dibutyl phthalate. The release rate per hour for this delivery system is seen in FIG. 5 wherein AGF is artificial gastric fluid and AIF is artificial intestinal fluid, and the amount of beclomethasone dipropionate is measured over 30 hours. Artificial gastric and artificial fluids are known in *The United States Pharmacopoeia*, Twentieth Revision, p 1105, published 1980.

EXAMPLE 3

A delivery device for delivering a therapeutic drug is made as follows: first, 22,642.85 grams of polyethylene oxide, having a molecular weight of about 300,000, and 1,250 grams of hydroxypropylmethylcellulose, having a molecular weight of 9,500, are dry screened through a Fitzmill® comminuter using a 35 mesh stainless steel screen, and then transferred to a Hobart® blender. Next, 107.15 grams of beclomethasone dipropionate is dissolved in anhydrous ethanol along with 1000 grams of polyvinylpyrrolidone. This granulating fluid is slowly added to the blender to produce a homogeneous blend. Next, the wet blend is passed through the comminuter using an 8 mesh stainless steel screen. The wet granules resulting from the screening process are dried in a forced air oven for about 18 hours at 30° C. Finally, the dry granules are passed through the comminuter using a 16 mesh stainless steel screen to yield the first composition comprising the drug beclomethasone dipropionate.

Next, the second composition is prepared as follows: 12,940 gram of polyethylene oxide, having a 5,000,000 molecular weight, 5,860 grams of sodium chloride, 1000 grams of hydroxypropylmethylcellulose, having a 11,300 molecular weight, and 200 grams of ferric oxide, are added to and passed through the comminuter using a 35 mesh stainless steel screen. The screened particles next are transferred to the blender and blend to produce a well mixed blend, and to the blending ingredients anhydrous ethanol is added as a granulating fluid. Next, the wet blend is transferred to the Fitzmill comminuter using a 7 mesh stainless steel screen. Then, the wet granules are transferred to drying sheets and dried in a forced air oven at 30° C. for about 18 hours. The dried granules are passed through the comminuter using a 16 mesh stainless steel screen to yield the second composition comprising means for pushing the first composition from the delivery device.

Next, the first composition and the second composition are pressed into a first layer and into a second layer in a tableting machine using a 3/16 inch punch and die. The first composition weighed 23 mg and it comprises 0.1000 mg of beclomethasone dipropionate, 1.1666 mg of hydroxypropylmethylcellulose, 21.1321 mg of the polyethylene oxide, and 0.9333 mg of the polyvinylpyrrolidone; the second composition comprises 10.784 mg of the polyethylene oxide coagulant, 4.8837 mg of sodium chloride, 0.8384 mg of hydroxypropylmethylcellulose and 0.1667 mg of ferric oxide.

Next, a semipermeable wall is applied around the compressed laminated compositions The wall forming composition comprises 97 wt % of cellulose triacetate having an acetyl content of 43.5%, and 3 wt % of polyethylene glycol 3350. The wall forming ingredients are dissolved in a cosolvent comprising 80:20 wt/wt methylene chloride-methanol comprising 5% solids. The wall is formed in an Accela-Cota pan coater to an approximate thickness of 3 mils (0.076 mm) to provide a coating weight of 5 mg. After drying, and removing the cosolvent, a 25 mil orifice is laser drilled in the semipermeable wall to the first composition.

Next, an outside exterior wall, comprising means for delaying the release of drug from the device during the devices' passage through an acidic environment, and for simultaneously preventing an exterior fluid from entering the device is coated onto the outside surface of the semipermeable, wall. The outside wall forming composition comprises 85 wt % of a copolymer of (methacrylic acid and methacrylic acid methyl ester, also known as Eudragit® S-100) and 15 wt % of hydrophobic cellulose acetyl phthalate for saturating the coat in 95% ethanol to provide 3% solids. The outside wall is applied in a 24 inch Accela-Cota® pan coater to apply a 3 mil (0.076 mm) wall.

The delivery devices made by the above procedure are dried in a humidity oven for 48 hrs at 50% relative humidity. Then, the delivery devices are dried an additional 24 hrs at 50° C in a forced air oven.

In another presently preferred embodiment, 5 delivery devices are encapsulated in a number 2 gelatin capsule. Each delivery device contains 0.100 mg (100 µg) of beclomethasone dipropionate and total delivery system delivers 500 µg of beclomethasone dipropionate to the intestine and colon.

EXAMPLE 4

The procedure described in Example 2 is followed with all conditions as set forth, except that in these examples the drug steroid is a member selected from the group consisting of beclomethasone, beclomethasone 17-propionate, beclomethasone 21-acetate, beclomethasone butyrate, and beclomethasone di propionate monohydrate.

EXAMPLE 5

Delivery device are made comprising salicylazosulphapyridine for treating Crohn's disease, and with an outer coat comprising a membrane selected from the group consisting of dimethylaminoethylmethacrylate-butylmethacrylate-methylmethacrylate copolymer of 150,000 molecular weight blended with a membrane selected from the group consisting of cellulose acetyl phthalate, cellulose diacetyl phthalate, dialkyl phthalate, cellulose triacetyl phthalate, cellulose acetate phthalate, hydroxypropylmethylcellulose phthalate, sodium cellulose acetate phthalate, cellulose ether phthalate, cellulose ester phthalate, and methylcellulose phthalate.

EXAMPLE 6

Delivery devices for delivering a drug are made according to the present examples wherein the drug is a member selected from the group consisting of hydrocortisone, prednisolone, prednisolone phosphate and prednisone, and wherein the exterior coat for delaying drug release in an acidic environment and for preventing water passage through the coat is a member selected from the group consisting of polymers of methacrylic acid and methacrylic acid methyl esters, methacrylic acid-ethylacrylate copolymer, and trimethylammonium ethylmethacrylatechloride-methylacrylate-ethylacrylate copolymer, blended with a hydrophobic member selected from the group consisting of cellulose acetyl phthalate, cellulose diacetyl phthalate, cellulose triacetyl phthalate, cellulose acetate phthalate, hydroxypropylmethylcellulose phthalate, sodium cellulose acetate phthalate, cellulose ether phthalate, cellulose ester phthalate, and methylcellulose phthalate:

EXAMPLE 7

The procedure of Example 1 is followed with the manufacturing procedures as previously set forth, except that the outside coat forming composition comprises 75 wt % of a copolymer of trimethyl ammonium ethylmethacrylate chloride-methylmethacrylate-ethylacrylate in the ratio of 5:65:3, 20 wt % dibutyl phthalate, and 5 wt % acetyltriethylcitrate, in 95% ethanol, to provide 3% solids, and the drug is 5-aminosalicylic acid.

DESCRIPTION OF METHOD OF PERFORMING THE INVENTION

A presently preferred embodiment of the invention pertains to a method for delivering a drug to the intestinal tract of a human at a controlled rate and continuously, which method comprise the steps of: (A) admitting orally into the humans gastrointestinal tract a dispensing device comprising: (1) a wall comprising an inside surface that surrounds and forms an internal compartment, said wall comprising a composition permeable to the passage of a biological fluid; (2) coating means on the outside surface of the wall for substantially preventing fluid access to the wall and, consequently, preventing the passage of fluid through the wall during the period of time the dispensing device passes through the stomach; (3) a drug means in the compartment for delivering drug to the intestine (4) means in the compartment for pushing the drug means from the device; (5) exit means in the device for delivering the drug from the device; (B) releasing the exterior coat means from the wall, (C) imbibing fluid through the wall into the compartment for converting the drug means into a dispensable formulation; (D) imbibing fluid into the compartment at a rate determined by the permeability of the wall and the osmotic pressure gradient across the wall, thereby causing the means for pushing to expand and push the drug dispensable formulation from the device; and (E) delivering the beneficial drug formulation from the compartment by the expandable means continuously expanding thereby causing the drug to be dispensed through the exit means at a therapeutically, effective amount at a controlled rate over a period of time to the intestinal tract of a human.

Inasmuch as the foregoing specification comprises preferred embodiments of the invention it is understood that variations and modifications may be made herein, in accordance with the inventive principles disclosed, without departing from the scope of the invention.

We claim:

1. An improvement in a device for delivering drug to the fluid environment of the gastrointestinal tract, wherein the device comprises:

(a) a wall comprising an exterior surface that faces the environment, said wall comprising a composition permeable to the passage of fluid, which wall surrounds;

(b) a compartment;

(c) a drug in the compartment;

(d) exit means in the wall for delivering the drug from the compartment;

(e) an enteric coat on the exterior wall surface which faces the fluid environment for substantially delaying the delivery of drug from the device, and wherein the improvement comprises;

(f) hydrophobic compound present in excess of its solubility in the exterior enteric coat which faces the fluid environment for substantially preventing the passage of fluid through the enteric coat.

2. The improvement in a device for delivering the drug to the fluid environment according to claim 1, wherein the hydrophobic compound is present in from 1 weight percent to 50 weight percent in the exterior enteric coat.

3. The improvement in a device for delivering the drug to the fluid environment according to claim 1, wherein the drug is a member selected from the group consisting of adrenocorticosteroid, hydrocortisone, prednisolone, prednisolone phosphate, prednisolone sulfate, prednisolone metasulpho-benzoate sodium, prednisolone sodium, prednisolone sodium phosphate, corticosteroid, beclomethasone, beclomethasone acetate, beclomethasone valerate, beclomethasone propionate, and beclomethasone dipropionate.

4. The improvement in the device for delivering the drug to the fluid environment of the gastrointestinal tract, according to claim 1, wherein the drug in the compartment comprises a member selected from the group consisting of salicylazosulfapyridine, hydrocortisone, prednisolone, prednisone, and cyclosporin.

5. An improvement in a device for delivering the drug to the fluid environment of the gastrointestinal tract, wherein the device comprises:
(a) a wall comprising an exterior surface that faces the environment, said wall comprising a composition permeable to the passage of fluid, which wall surrounds;
(b) a compartment;
(c) a drug in the compartment;
(d) exit means in the wall for delivering the drug from the compartment;
(e) an enteric coat on the exterior wall surface which faces the fluid environment for substantially delaying the delivery of drug from the device, and wherein the improvement comprises;
(f) a hydrophobic compound present in excess of its solubility in the exterior enteric coat which faces the fluid environment for substantially preventing the passage of fluid through the enteric coat, which hydrophobic compound comprises a member selected from the group consisting of ethylmethacrylate-butylmethacrylate-methylmethacrylate copolymer, methacrylic acid-methylmethacrylate copolymer trimethylammoniumethyl-methacrylatechloride-methylmethacrylate-ethylacrylate copolymer, and ethylacryylate-methylmethacrylate copolymer.

* * * * *